United States Patent [19]
Tremblay et al.

[11] Patent Number: 5,704,352
[45] Date of Patent: Jan. 6, 1998

[54] IMPLANTABLE PASSIVE BIO-SENSOR

[76] Inventors: Gerald F. Tremblay, 13015 St. Andrew Dr., Kansas City, Mo. 64145; David S. Buckles, 121 W. 48th St. -Apt. 1705, Kansas City, Mo. 64112

[21] Appl. No.: 562,093

[22] Filed: Nov. 22, 1995

[51] Int. Cl.$^6$ .................................................. A61B 5/00
[52] U.S. Cl. .................. 128/630; 128/748; 128/675; 128/642; 128/673
[58] Field of Search .................. 128/630, 642, 128/748, 675, 673, 903, 899

[56] References Cited

U.S. PATENT DOCUMENTS

| | | |
|---|---|---|
| 3,757,770 | 9/1973 | Brayshaw et al. |
| 3,853,117 | 12/1974 | Murr. |
| 4,026,276 | 5/1977 | Chubbuck. |
| 4,062,354 | 12/1977 | Taylor et al. |
| 4,127,110 | 11/1978 | Bullara. |
| 4,206,761 | 6/1980 | Cosman. |
| 4,206,762 | 6/1980 | Cosman. |
| 4,265,252 | 5/1981 | Chubbuck et al. |
| 4,281,666 | 8/1981 | Cosman. |
| 4,281,667 | 8/1981 | Cosman. |
| 4,340,038 | 7/1982 | Mc Kean. |
| 4,354,506 | 10/1982 | Sakaguchi et al. |
| 4,378,809 | 4/1983 | Cosman. |
| 4,385,636 | 5/1983 | Cosman. |
| 4,471,786 | 9/1984 | Inagaki et al. |
| 4,519,401 | 5/1985 | Ko et al. |
| 4,593,703 | 6/1986 | Cosman. |
| 4,653,508 | 3/1987 | Cosman. |
| 4,660,568 | 4/1987 | Cosman. |
| 4,676,255 | 6/1987 | Cosman. |
| 4,885,002 | 12/1989 | Watanabe et al. |
| 4,911,217 | 3/1990 | Dunn et al. |
| 5,074,310 | 12/1991 | Mick. |
| 5,117,835 | 6/1992 | Mick. |
| 5,218,861 | 6/1993 | Brown et al. |
| 5,291,899 | 3/1994 | Watanabe et al. |
| 5,423,334 | 6/1995 | Jordan. |
| 5,445,150 | 8/1995 | Dumoulin et al. ............... 128/899 |

OTHER PUBLICATIONS

IEEE Transactions on Biomedical Engineering, vol. 42, No. 5, May, 1995, Title: Data Transmission from an Implantable Biotelemeter by Load-Shift Keying Using Circuit Configuration Modulator, by Zhengnian Tang, Brian Smith, John H. Schild, and P. Hunter Peckham, pp. 524–528.

Neurosurgery, vol. 34, No. 5, May, 1994, Concepts and Innovations, Title: A New Ventricular Catheter for the Prevention and Treatment of Proximal Obstruction in Cerebrospinal Fluid Shunts, by Enrique C.G. Ventureyra, M.D., F.R.C.S.(C)., F.A.C.S., Michael J. Higgins, M.D., pp. 924–926.

Neurosurgery, vol. 34, No. 6, Jun. 1994, Rapid Communication, Title: The Use of the Codman–Medos Programmable Hakim Valve in the Management of Patients with Hydrocephalus: Illustrative Cases, by Peter McL. Black, M.D., Ph.D., Rodolfo Hakim, M.D., Nancy Olsen Bailey, R.N., B.S.N., M.B.A., pp. 1110–1113.

(List continued on next page.)

*Primary Examiner*—Jennifer Bahr
*Assistant Examiner*—Stephen Huang
*Attorney, Agent, or Firm*—Hovey, Williams, Timmons & Collins

[57] ABSTRACT

An implantable, passive bio-sensor (10) for monitoring internal physiological conditions of a patient is disclosed. The bio-sensor (10) includes at least one sensor or transducer (12) for monitoring a physiological condition of the patient and a passive transponder (14) that receives sensor signals from the sensor or sensors (12), digitizes the sensor signals, and transmits the digitized signals out of the patient's body when subjected to an externally generated interrogation signal. In one embodiment, the bio-sensor (100) is incorporated into the sidewall of a shunt (102) used for treating hydrocephalus for non-invasively monitoring the operation of the shunt (102).

24 Claims, 2 Drawing Sheets

OTHER PUBLICATIONS

Neurosurgery Clinics of North America vol. 4, No. 4, Oct., 1993, Hydrocephalus, Title: The Treatment of Hydrocephalus by Paul M. Kanev, MD, and T.S. Park, MD.

Neurosurgery Clinics of North America, vol. 4, No. 4, Oct., 1993, Hydrocephalus, Title: Complications in Ventricular Cerebrospinal Fluid Shunting by Jeffrey P. Blount, MD, John A. Campbell, MD, and Stephen J. Haines, MD, pp. 633–636.

Neurosurgery Update II Vascular, Spinal, Pediatric, and Functional Neurosurgery, Published by McGraw-Hill, Inc., Editors Robert H. Wilkins, M.D., and Setti S. Rengachary, M.D., Title Shunt Systems by Elisabeth M. Post, pp. 300–319.

Pediatric Neurosurgery 2nd Edition, Surgery of the Developing Nervous System, Published by W.B. Saunders Company Harcourt Brace Jovanovich, Inc., Title: Treatment of Hydrocephalus by Harold L. Rekate, M.D., pp. 200–229.

IMPLANTABLE PASSIVE BIO-SENSOR

BACKGROUND OF THE INVENTION

1. Field of the Invention

The present invention relates to implantable medical devices for monitoring internal physiological conditions of a patient, and more particularly to a bio-sensor for implantation in a patient that includes at least one sensor for monitoring a physiological condition of the patient and a passive transponder that receives sensor signals from the sensor or sensors, digitizes the sensor signals, and transmits the digitized signals together with a unique device identification code out of the patient's body when subjected to an externally generated interrogation signal. The invention also relates to a bio-sensor that includes a shunt and a monitoring device embedded in the walls of the shunt for permitting identification and non-invasive testing of the operation of the shunt.

2. Description of the Prior Art

Many medical conditions require the monitoring and measurement of internal physiological conditions of a patient. For example, hydrocephalus, which is a brain condition where cerebrospinal fluid accumulates at abnormally high pressures in ventricles or chambers of a patient's brain, may require monitoring of the intracranial fluid pressure of the patient.

Implantable devices for monitoring internal physiological conditions of a patient are known in the art. One such prior art device includes an implantable pressure transducer that transmits pressure signals out of the patient by means of a wire passing through the patient's skull. These types of devices are generally unsatisfactory due to increased risk of infection and patient discomfort caused by the externally extending wire.

Monitoring devices that are completely implantable within a patient are also known in the art. One such prior art device includes a sensor for sensing a physiological condition of the patient and a transmitter and battery assembly for transmitting the sensor signals out of the patient's body. These types of devices are also unsatisfactory for many types of medical conditions since the batteries are bulky and must be periodically replaced, thus necessitating additional surgery.

Implantable monitoring devices that do not require batteries have also been developed. One such device employs sensors coupled with frequency tuned L-C circuits. The sensors mechanically translate changes in sensed physiological condition to the inductor or capacitor of the tuned L-C circuit for changing the reactance of the L-C circuit. This change in reactance alters the resonant frequency of the circuit, which is then detected by an external transmitter and converted to a signal representative of the monitored physiological condition.

Although these L-C type implantable monitoring devices are superior to battery operated devices in some respects, they also suffer from several limitations that limit their utility. For example, the L-C circuits are difficult to calibrate once implanted, are inherently single-channel, and are only sensitive in a particular range of measurements. Thus, L-C type monitoring devices are not always accurate after they have been implanted for a long period of time and are not suitable for use with sensors that have a wide sensing range.

A general limitation of all the above-described prior art implantable monitoring devices is that they are operable for sensing or monitoring only one physiological condition. Thus, if a doctor wishes to monitor both the pressure in the ventricles of a patient's brain and the temperature of the fluid in the ventricles, two of these prior art monitoring devices must be implanted in the patient.

A further limitation of prior art implantable devices is that they merely monitor a physiological condition of the patient and transmit a signal representative of the condition out of the patient's body, but do not perform any processing or conversion of the signals.

Another limitation of prior art implantable monitoring devices is that they are operable only for monitoring physiological conditions but not for alleviating the underlying cause of the physiological condition. For example, intracranial pressure sensors designed for use with patients suffering from hydrocephalus merely detect when fluid pressure levels within the patient's brain are high, but are not operable for reducing the amount of cerebrospinal fluid accumulated in the patient's brain. Thus, once these prior art intracranial pressure sensors determine that the pressure in the patient's brain is too high, surgery must be performed to alleviate the condition.

Cerebrospinal fluid shunts can be implanted in the patient for draining cerebrospinal fluid from the patient's brain, but these shunts can become clogged during use. Thus, it is necessary to frequently monitor the operation of the shunt to ensure that the shunt is properly draining cerebrospinal fluid from the patient's brain. Currently, the only known method to determine if a shunt is clogged is to insert a needle through the patient's skin and into the shunt. Since this type of testing is invasive and expensive, it is painful, somewhat risky, and sometimes requires surgery.

OBJECTS AND SUMMARY OF THE INVENTION

In view of the foregoing, it is an object of the present invention to provide a bio-sensor for monitoring one or more physiological conditions of a patient that is completely implantable beneath the patient's skin.

It is another object of the present invention to provide a bio-sensor that requires no batteries or other internal sources of power.

It is another object of the present invention to provide a bio-sensor that accurately measures physiological conditions over all measurement ranges and does not require re-tuning once implanted in a patient.

It is another object of the present invention to provide a bio-sensor that is operable for monitoring a plurality of physiological conditions and for processing the signals associated with the monitoring of the physiological conditions before transmission from the patient.

It is another object of the present invention to provide a bio-sensor that permits non-invasive testing of the operation of a shunt.

It is another object of the present invention to provide a bio-sensor that is embedded in a cerebrospinal fluid shunt for implantation in a patient for simultaneously draining cerebrospinal fluid from the patient's brain for treating the patient's hydrocephalus and for monitoring and non-invasively testing the operation of the shunt.

It is another objective of the present invention to transmit a unique device identification code which can be used as an aid in tracking patient history.

In view of these objects and other objects that become evident from the description of the preferred embodiments of the invention herein, an improved bio-sensor is provided. The bio-sensor is completely implantable in a patient. The bio-sensor requires no batteries or other sources of internal power and is therefore passive.

One embodiment of the bio-sensor broadly includes one or more sensors or transducers for sensing one or more physiological conditions of the patient and a transponder for receiving signals from the sensors and for transmitting the signals out of the patient's body when subjected to an externally generated interrogation signal.

In more detail, the transponder includes processor means and transmitting means. The processor means receives the sensor signals from the sensors and converts the signals to a digital format. The processor may also be programmed to analyze the signals for performing calculations described below. The transmitting means is coupled with the processor means for transmitting the digital signals out of the patient's body when subjected to an interrogation signal from an external interrogating device.

In a second embodiment of the invention, the bio-sensor includes a shunt for draining fluid from a portion of a patient's body and a monitoring means embedded within the walls of the shunt for non-invasively monitoring the operation of the shunt. In preferred forms, the shunt is a cerebrospinal fluid shunt for draining cerebrospinal fluid from a patient's brain. The cerebrospinal fluid shunt includes a ventricular end and an axially opposed distal end connected by a sidewall defining a fluid passageway.

The ventricular end is placed in a ventricular cavity of the patient's brain, and the distal end is placed in an organ or body cavity remote from the patient's brain for draining cerebrospinal fluid out of the shunt.

The monitoring means is embedded in the sidewall of the cerebrospinal fluid shunt and includes one or more pressure sensors for sensing the pressure of the cerebrospinal fluid in the shunt passageway and a transponder for receiving pressure signals from the pressure sensors and for transmitting the signals out of the patient's body when subjected to an externally generated interrogation signal.

By constructing a bio-sensor in accordance with the preferred embodiments of the invention as described herein, numerous advantages are realized. For example, by providing a bio-sensor that is completely implantable beneath the patient's skin, risks of infections and patient discomfort caused by prior art partially implantable bio-sensor devices are greatly reduced.

Additionally, by providing a bio-sensor that transmits signals from the patient's body only after interrogated by an external interrogation device, physiological conditions can be monitored passively without the use of batteries or other internal sources of power.

Additionally, by providing a bio-sensor that does not employ tuned L-C circuits, physiological conditions can be accurately measured over all measurement ranges without re-tuning the sensor once implanted in a patient.

Additionally, by providing a bio-sensor that is operable for monitoring a plurality of physiological conditions and for converting the signals to digital format, the monitored signals can be analyzed before transmission out of the patient's body. For example, sensors can be provided for monitoring both the pressure and temperature of the cerebrospinal fluid in the patient's brain. The processor can then analyze the signals to adjust the pressure signal transmitted out of the patient's body to compensate for abnormally high or low temperature readings, since temperature affects the measured pressure signals.

Additionally, by providing a bio-sensor that is incorporated or embedded in a cerebrospinal fluid shunt for implantation in a patient, the bio-sensor is operable for simultaneously draining cerebrospinal fluid from the patient's brain for treating the patient's hydrocephalus and for monitoring and non-invasively testing the functioning of the shunt. Thus, the operation of the shunt can be easily and painlessly tested without invasive surgical procedures.

Additionally, provision of a unique device identification code allows for tracking of a patient history, e.g., for correlation of measurements made from the same device, but at different times and/or at different locations or facilities.

BRIEF DESCRIPTION OF THE DRAWING FIGURES

A preferred embodiment of the present invention is described in detail below with reference to the attached drawing figures, wherein.

Figure 2:
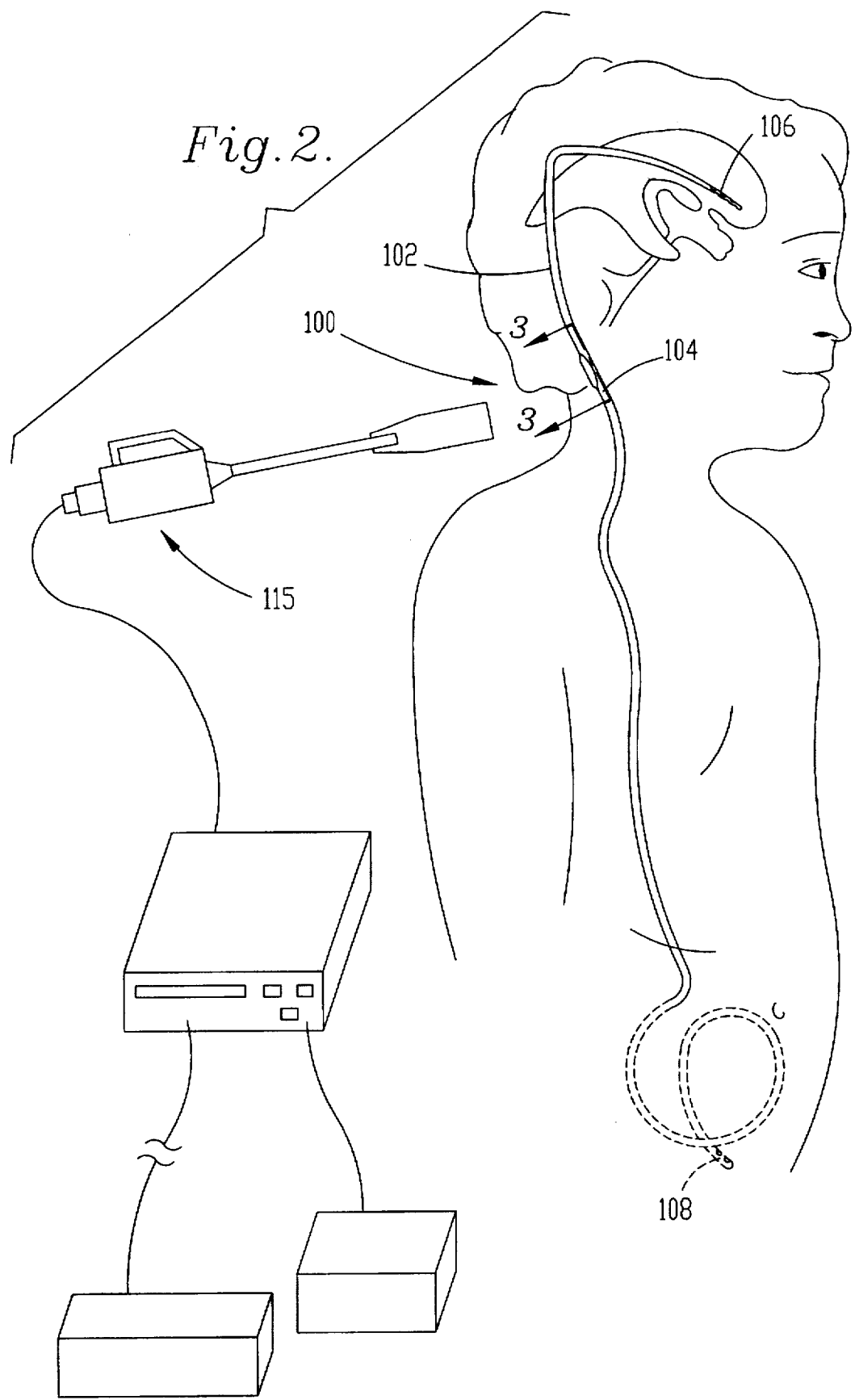
FIG. 2 is a schematic view of a bio-sensor constructed in accordance with a second embodiment of the invention shown implanted in a patient.

FIG. 3 a section view of the bio-sensor of the second embodiment taken along line 3—3 of FIG. 2; and FIG. 4 an elevational view of the monitoring unit of the second embodiment of the invention shown removed from the shunt.

DETAILED DESCRIPTION OF THE PREFERRED EMBODIMENTS

EMBODIMENT OF FIG. 1

Figure 1:
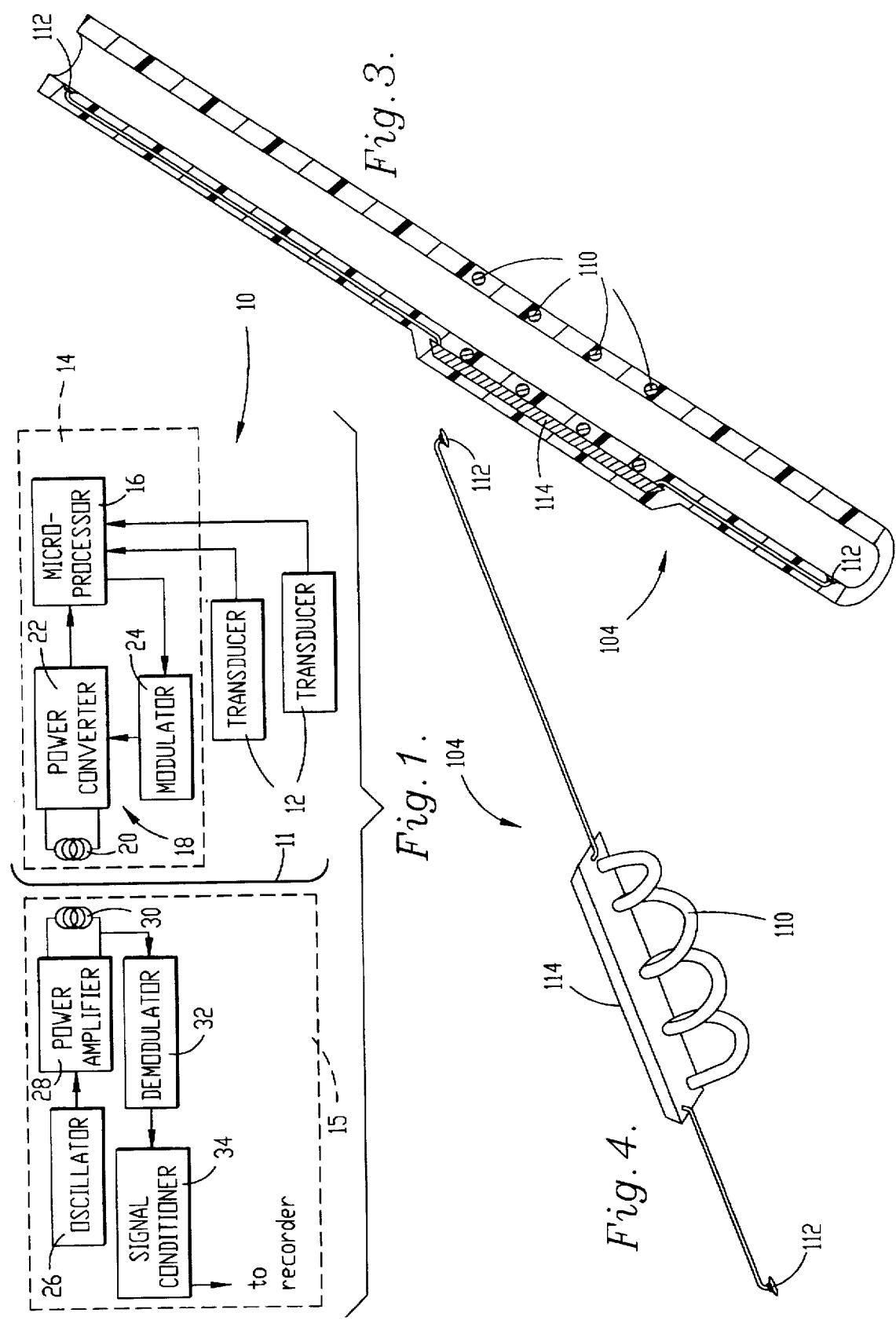
FIG. 1 is a block diagram of a bio-sensor constructed in accordance with a first embodiment of the invention.

Referring to FIG. 1, a bio-sensor 10 constructed in accordance with a first preferred embodiment of the invention is illustrated. In use, the bio-sensor 10 is implanted beneath a patient's skin 11 for sensing or monitoring one or more physiological conditions of the patient and for transmitting signals out of the patient's body representative of these physiological conditions.

As illustrated, the bio-sensor 10 broadly includes one or more sensors or transducers 12 for sensing, monitoring or measuring one or more physiological conditions of the patient and a transponder 14 for receiving signals from the transducers 12 and for transmitting the signals out of the patient's body when subjected to an externally generated interrogation signal. The externally generated interrogation signal is generated by an interrogator 15 illustrated in FIG. 1 and described in more detail below.

The sensors or transducers 12 are operable for monitoring or detecting one or more physiological conditions within the patient such as the pressure of cerebrospinal fluid in cavities or ventricles of the patient's brain. The sensors or transducers 12 then generate sensor signals representative of these measured physiological conditions. The sensor signals are typically analog signals but may also be digital.

The transducers 12 are conventional in construction and may include pressure transducers, temperature sensors, pH sensors, blood sugar sensors, blood oxygen sensors, or any other type of physiological sensing, monitoring or measuring devices responsive to motion, flow, velocity, acceleration, force, strain, acoustics, moisture, osmolarity, light, turbidity, radiation, electromagnetic fields, chemicals, ionic, or enzymatic quantities or changes. Examples of these and other sensor devices useful in the present invention are described in detail in the *AIP Handbook of Modern Sensors* by Jacob Fraden, hereby incorporated by reference. In preferred forms, the transducers 12 are pressure transducers such as the MPX2000 series devices manufactured by Motorola.

The transponder 14 is electrically coupled with the sensors 12 for receiving the sensor signals. In general, the transponder 14 converts the sensor signals to digital, analyzes the sensor signals, and transmits the converted and analyzed signals out of the patient's body when subjected to an interrogation signal from the interrogator 15.

Returning to FIG. 1, the transponder 14 preferably includes a microprocessor 16 and a transmitting assembly 18. The components of the transponder 14 can be formed from separate integrated circuit devices, but are preferably formed on a single integrated circuit chip that integrates the functions of all the components.

In more detail, the microprocessor 16 is electrically coupled with the transducers 12 with conventional conductive wires for receiving the sensor signals from the transducers 12. The microprocessor 16 may receive sensor signals via a serial or parallel connection with the transducers 12.

The microprocessor 16 converts the analog signals from the transducers 12 to digital signals and formats the digitized signals as a binary data stream for transmission out of the patient. The microprocessor 16 is also operable for coding and formatting a unique device ID number for transmission with the digitized transducer signals for use in identifying the transponder 14 and transducers 12. An example of a microprocessor 16 that may be used with the invention is device number P1C16C71 manufactured by MicroChip.

In preferred forms the microprocessor 16 can be programmed for analyzing the monitored signals before transmitting the signals out of the patient's body. For example, if the bio-sensor 10 is provided with a pressure transducer and a temperature sensor for measuring both the pressure and temperature of the cerebrospinal fluid in the patient's brain, the processor 16 can be programmed to adjust the pressure signal transmitted out of the patient's body to compensate for abnormally high or low temperature readings sensed by the temperature sensor. In this way, the bio-sensor 10 can provide more accurate pressure reading since pressure is highly dependent on temperature.

The transmitting assembly 18 is coupled with the microprocessor 16 for receiving the digitized signals from the microprocessor 16 and for transmitting the signals out of the patient's body when subjected to an interrogation signal from the interrogator 15. In the preferred embodiment, the transmitting assembly 18 employs load-shift keying data transmission techniques described in the article *Data Transmission from An Implantable Biotelemeter by Load-Shift Keying Using Circuit Configuration Modulator*, by Zhengnian Tang, Brian Smith, John H. Schild, and P. Hunter Peckham, published in the IEEE Transaction on Biomedical Engineering, Volume 42, No. 5, May, 1995. This article is hereby incorporated by reference. Load-shift keying allows simultaneous powering or energizing of the transponder 14 and data transmission from the transponder 14 through the same radio frequency (RF) inductive couple.

As illustrated in FIG. 1, the transmitting assembly 18 preferably includes an antenna or coil 20, a power converter 22, and a modulator 24. The antenna or coil 20 is inductively or electromagnetically coupled with an antenna or coil 30 in the interrogator 15 as described below for receiving interrogation signals from the interrogator 15. The antenna or coil 20 is preferably formed from conductive material such as metallic wire, carbon fiber wires, conductive ink, conductive elastomeric materials, or other conventional inductor materials.

The power converter 22 is coupled with the antenna 20 for extracting energy from the inductive or electromagnetic couple with the interrogator 15. The power converter 22 converts this electromagnetic energy to a current signal for powering the microprocessor 16.

The modulator 24 is coupled with the microprocessor 16 and the power converter 22 for receiving the digitized data from the microprocessor 16 and for modulating the interrogation signal in accordance with the digital data stream to create a modulated interrogation signal. The modulator 16 alters the electronic characteristics of the electromagnetic coupling between the interrogator antenna 30 and the implantable device antenna 20 in a manner which effects a modulation of the interrogator signal. The modulation of the interrogator signal is detectable at the interrogator 15, and the modulation pattern reflects accurately the information content of the digital data stream which was routed from the microprocessor 16 to the modulator 24. The modulation technique employed in the preferred form is load-shift keying, however any equivalent technique such as frequency-shift keying or phase-shift keying may be employed. In this manner, digitized data are conveyed from the implanted transponder 14 to the interrogator 15 without physical contact.

The interrogator 15 is provided for simultaneously energizing the implanted transponder 14 and for receiving or detecting the shifts in the characteristic frequency of the transponder antenna 20 caused by the modulator 24. As illustrated in FIG. 1, the preferred interrogator 15 includes an oscillator 26, a power amplifier 28, an antenna or coil 30, a demodulator 32, and a signal conditioner 34.

The oscillator 26 and power amplifier 28 provide energy to the antenna 30 for powering the transponder 14. The oscillator 26 also provides a carrier frequency to the antenna 30 for modulation by the transponder modulator 24 for data transmission. The oscillator 26 and power amplifier 28 may be any known devices, including devices constructed in accordance with the IEEE article referenced above.

The antenna 30 is electrically coupled with the power amplifier 28 and inductively or electromagnetically coupled with the antenna 20 of the implanted transponder 14. The antenna 30 delivers the electromagnetic energy generated by the oscillator 26 and power amplifier 28 to the transponder 14 and detects the shifts in the characteristics of the antenna 20 caused by the transponder modulator 24. The antenna or coil 30 is similar to the transponder antenna 20 and is formed from a cylindrical coil of conductive material such as metallic wire, carbon fiber wires, conductive ink, conductive elastomeric materials, or other conventional coil materials.

The demodulator 32 is coupled with the interrogator antenna 30 and is provided for extracting digital data from the carrier signal detected by the antenna 30. An example of a demodulator 32 that can be used in the interrogator 15 of the present invention is the type MC1496 or MC1596 demodulator manufactured by Motorola.

The signal conditioner 34 is coupled with the demodulator 32 for converting the demodulated data to a format suitable for recording or storing in external devices. An example of a signal conditioner 34 that can be used in the interrogator 15 of the present invention is the type ADM202 conditioner manufactured by Analog Devices. The signal conditioner 34 may also be coupled with conventional recording and/or analyzing devices such as computers, printers, and displays for recording and analyzing the signals transmitted out of the bio-sensor 10.

In use, the bio-sensor 10 described herein is implanted in a patient for sensing, monitoring or detecting one or more physiological conditions of the patient. When it is desired to collect or analyze the signals generated by the transducers 12 of the bio-sensor 10, the interrogator 15 is placed adjacent the portion of the patient's body in which the bio-sensor 10 is implanted. The interrogator 15 generates an interrogation signal for simultaneously powering the bio-sensor 10 and for retrieving the digitized signals from the transponder 14. The interrogator 15 then demodulates the digitized signals and delivers the signals to the recording and analyzing devices described above.

EMBODIMENT OF FIGS. 2-4

Referring to FIGS. 2-4, a second preferred embodiment of the invention is illustrated. As best illustrated in FIG. 2, the bio-sensor 100 of this embodiment broadly includes a shunt 102 for draining fluid from a portion of a patient's body and a monitoring device 104 embedded within the walls of the shunt 102 for non-invasively monitoring the operation of the shunt 102.

In more detail, the preferred shunt 102 is a cerebrospinal fluid shunt for draining cerebrospinal fluid from a patient's brain. The cerebrospinal fluid shunt 102 is preferably formed of medical grade synthetic resin material and presents opposed ventricular 106 and distal ends 108 connected by a fluid passageway. When the shunt 102 is implanted in a patient, the ventricular end 106 is positioned in a ventricular cavity of the patient's brain and the distal end 108 is positioned in an organ or body cavity remote from the ventricular cavity such as the patient's abdomen for draining cerebrospinal fluid out of the patient's brain.

As best illustrated in FIG. 3, the monitoring device 104 is preferably formed or embedded within the sidewall of the cerebrospinal fluid shunt 102. Referring to FIG. 4, the monitoring device 104 preferably includes one or more pressure sensors or transducers 112 and a transponder 114 electrically coupled with the transducers 112. The monitoring device may alternatively include temperature sensors, pH sensors, blood sugar sensors, blood oxygen sensors, or any other type of physiological sensing, monitoring or measuring devices responsive to motion, flow, velocity, acceleration, force, strain, acoustics, moisture, osmolarity, light, turbidity, radiation, electromagnetic fields, chemicals, ionic, or enzymatic quantities or changes.

The preferred pressure transducers 112 are provided for sensing the pressure of the cerebrospinal fluid in the shunt passageway and are preferably spaced a distance apart from one another for sensing pressure at different points within the passageway. The pressure transducers 112 may be placed anywhere in the shunt 102 and may include piezoresistive transducers, silicone capacitive pressure transducers, variable-resistance laminates of conductive ink, variable conductants elastomeric devices, strain gauges or similar type pressure sensitive devices.

The transponder 114 is also preferably formed or embedded within the sidewall of the shunt 102 and is coupled with the pressure transducers 112 for receiving pressure signals therefrom. The transponder 114 is identical to the transponder 12 disclosed in the first embodiment of the invention except that its antenna or coil 110 is embedded within the sidewall of the shunt 102.

In use, the bio-sensor 100 of the second embodiment of the invention is implanted in a patient as illustrated generally in FIG. 2 for draining or removing cerebrospinal fluid from the patient's brain for treating hydrocephalus. The monitoring device 104 formed with the sidewall of the shunt 102 senses or detects the pressure of the cerebrospinal fluid in the shunt 102 and delivers pressure signals to the transponder 114.

When it is desired to collect or analyze the pressure signals generated by the transducers 112, an interrogator device 115 similar or identical to the interrogator 15 described in the first embodiment of the invention is placed adjacent the portion of the patient's body in which the bio-sensor 100 is implanted. The interrogator 115 generates an interrogation signal for simultaneously powering the bio-sensor 100 and for retrieving the digitized signals from the transponder 114.

Although the invention has been described with reference to the preferred embodiment illustrated in the attached drawing figures, it is noted that equivalents may be employed and substitutions made herein without departing from the scope of the invention as recited in the claims.

Having thus described the preferred embodiment of the invention, what is claimed as new and desired to be protected by Letters Patent includes the following:

1. A bio-sensor for implantation in a patient, said bio-sensor comprising:

sensor means for sensing a physiological condition of the patient and for generating a sensor signal representative of the physiological condition; and a transponder electrically coupled with said sensor means, said transponder including processor means for implanatation in the patient and responsive to said sensor means for converting said sensor signal to a digital signal representative of the physiological condition without sending said sensor signal out of the patient's body, and transmitting means coupled with said processor means for transmitting said digital signal out of the patient's body, said transmitting means including antenna means for receiving an interrogation signal generated from outside the patient and power converting means coupled with said antenna means for converting the interrogation signal to a power signal for energizing said processor means.

2. The bio-sensor as set forth in claim 1, said transmitting means further including modulating means coupled with said processor means and said antenna means for modulating said interrogation signal in accordance with said digital signal to create a modulated interrogation signal for transmitting said digital signal out of the patient.

3. The bio-sensor as set forth in claim 2, wherein said processor means, modulating means and power converting means are formed on an integrated circuit microprocessor chip.

4. The bio-sensor as set forth in claim 2, further including an interrogator positioned outside the patient's body for energizing said processor means, said interrogator including generating means for generating said interrogation signal, and transmitting means coupled with said generating means for transmitting said interrogation signal to said transponder and for receiving said modulated interrogation signal from said transponder.

5. The bio-sensor as set forth in claim 4, said interrogator further including demodulating means coupled with said transmitting means for demodulating said modulated interrogation signal to retrieve said digital signal.

6. The bio-sensor as set forth in claim 1, said sensor means including a plurality of sensors, each of said sensors being operable for sensing a separate physiological condition of the patient and for generating a corresponding sensor signal representative of its respective physiological condition.

7. The bio-sensor as set forth in claim 6, said processor means including signal receiving means for receiving a plurality of sensor signals from said sensors.

8. The bio-sensor as set forth in claim 7, said processor means including memory means for storing said plurality of sensor signals and analyzing means for analyzing said plurality of sensor signals.

9. The bio-sensor as set forth in claim 1, wherein said processor means is programmable.

10. The bio-sensor as set forth in claim 9, said processor means including a programmable microprocessor.

11. The bio-sensor as set forth in claim 1 further including a shunt presenting a tubular sidewall and opposed ends, wherein said sensor means and said transponder are embedded in said shunt sidewall.

12. The bio-sensor as set forth in claim 1, said sensor means including a sensor selected from the group consisting of a pressure sensor, a temperature sensor, a pH sensor, a blood sugar sensor, a blood oxygen sensor, a motion sensor, a flow sensor, a velocity sensor, an acceleration sensor, a force sensor, a strain sensor, an acoustics sensor, a moisture sensor, an osmolarity sensor, a light sensor, a turbidity sensor, a radiation sensor, an electromagnetic field sensor, a chemical sensor, an ionic sensor, and an enzymatic sensor.

13. The bio-sensor as set forth in claim 1, said transponder further including means for transmitting an identification code identifying said transponder out of the patient's body.

14. A bio-sensor for implantation in a patient, said bio-sensor comprising:

a shunt for draining fluid from a portion of a patient's body; and monitoring means coupled with said shunt for non-invasively monitoring said shunt, said monitoring means including sensor means for sensing a physiological condition of the patient and for generating a sensor signal representative of the physiological condition; and a transponder electrically coupled with said sensor means, said transponder including processor means for implantation in the patient and responsive to said sensor means for converting said sensor signal to a digital signal representative of the physiological condition, and transmitting means coupled with said processor means for transmitting said digital signal out of the patient's body, said transmitting means including antenna means for receiving an interrogation signal generated from outside the patient and power converting means coupled with said antenna means for converting the interrogation signal to a power signal for energizing said processor means.

15. The bio-sensor as set forth in claim 14, said transmitting means further including modulating means coupled with said processor means and said antenna means for modulating said interrogation signal in accordance with said digital signal to create a modulated interrogation signal for transmitting said digital signal out of the patient.

16. The bio-sensor as set forth in claim 14, said sensor means including a sensor selected from the group consisting of a pressure sensor, a temperature sensor, a pH sensor, a blood sugar sensor, a blood oxygen sensor, a motion sensor, a flow sensor, a velocity sensor, an acceleration sensor, a force sensor, a strain sensor, an acoustics sensor, a moisture sensor, an osmolarity sensor, a light sensor, a turbidity sensor, a radiation sensor, an electromagnetic field sensor, a chemical sensor, an ionic sensor, and an enzymatic sensor.

17. The bio-sensor as set forth in claim 14, said shunt including a cerebrospinal fluid shunt for draining cerebrospinal fluid from the patient's brain, said shunt presenting a tubular sidewall defining a fluid passageway, a ventricular end for placement in a ventricular cavity of the patient's brain for delivering cerebrospinal fluid to said passageway and a distal end axially opposed from said ventricular end for placement out of the ventricular cavity for draining cerebrospinal fluid out of said passageway.

18. The bio-sensor as set forth in claim 17, said sensor means including a first pressure sensor positioned within said fluid passageway for sensing the pressure of the cerebrospinal fluid in said fluid passageway and for generating a first pressure signal representative of the pressure.

19. The bio-sensor as set forth in claim 18, wherein said first pressure sensor is coupled with said ventricular end for sensing the pressure of the cerebrospinal fluid entering said shunt, said monitoring means further including a second pressure sensor coupled with said distal end for sensing the pressure of the cerebrospinal fluid flowing from said shunt and for generating a second pressure signal representative of the pressure.

20. The bio-sensor as set forth in claim 19, said processor means including receiving means for receiving said first and second pressure signals from said first and second pressure sensors.

21. The bio-sensor as set forth in claim 20, said processor means including calculating means for calculating the flow of cerebrospinal fluid through said shunt in response to receipt of said first and second pressure signals by said receiving means.

22. The bio-sensor as set forth in claim 20, said processor means including a programmable microprocessor.

23. The bio-sensor as set forth in claim 14, further including an interrogator positioned outside the patient's body for energizing said processor means, said interrogator including generating means for generating said interrogation signal, and transmitting means coupled with said generating means for transmitting said interrogation signal to said transponder and for receiving said modulated interrogation signal from said transponder.

24. The bio-sensor as set forth in claim 23, said interrogator further including demodulating means coupled with said transmitting means for demodulating said modulated interrogation signal to retrieve said digital signal.

* * * * *